United States Patent
Hopkins (10) Patent No.: US 11,311,174 B2
(45) Date of Patent: Apr. 26, 2022

(54) IMAGING SCOPE WITH LEAK INDICATOR, AND RELATED IMAGING SYSTEM AND METHOD

(71) Applicant: Karl Storz Endovision, Inc., Charlton, MA (US)

(72) Inventor: Vernon Hopkins, Charlton, MA (US)

(73) Assignee: Karl Storz Endovision, Inc., Charlton, MA (US)

(*) Notice: Subject to any disclaimer, the term of this patent is extended or adjusted under 35 U.S.C. 154(b) by 191 days.

(21) Appl. No.: 16/037,605

(22) Filed: Jul. 17, 2018

(65) Prior Publication Data
US 2020/0022561 A1  Jan. 23, 2020

(51) Int. Cl.
*A61B 1/00* (2006.01)
*G01M 3/06* (2006.01)
*A61B 1/12* (2006.01)

(52) U.S. Cl.
CPC ...... *A61B 1/00057* (2013.01); *A61B 1/00128* (2013.01); *G01M 3/06* (2013.01); *A61B 1/121* (2013.01)

(58) Field of Classification Search
CPC ............ G01M 3/02; G01M 3/26; G01M 3/32; G01M 3/3236; G01M 3/3263; A61B 1/00057; A61B 1/00128; A61B 1/121
USPC .......................................................... 73/40
See application file for complete search history.

(56) References Cited

U.S. PATENT DOCUMENTS

| | | |
|---|---|---|
| 4,506,544 A | 3/1985 | Shimizu |
| 4,527,551 A | 7/1985 | Ishii |
| 6,364,827 B1 | 4/2002 | Irion et al. |
| 6,412,334 B1 | 7/2002 | Kral et al. |
| 9,513,180 B2 | 12/2016 | Rowe et al. |
| 2006/0196250 A1 | 9/2006 | Gocho |
| 2011/0301414 A1 | 12/2011 | Hotto et al. |
| 2012/0000272 A1 | 1/2012 | Soriano Romero |
| 2014/0238110 A1 | 8/2014 | Williams |
| 2018/0271356 A1* | 9/2018 | Antonioli ........... A61B 1/00016 |

OTHER PUBLICATIONS

Extended European Search Report Application No. 19186869.4 Completed: Oct. 28, 2019; dated Nov. 7, 2019 7 Pages.

* cited by examiner

*Primary Examiner* — Benjamin R Schmitt
(74) *Attorney, Agent, or Firm* — Whitmyer IP Group LLC (57) ABSTRACT

An imaging scope includes an internal surface defining an internal cavity, a window permitting visual inspection of the internal cavity, a fluid in the internal cavity having a pressure different than ambient pressure, and a leak indicator transitionable between nonvisible and visible through the window when the pressure of the fluid changes toward ambient pressure.

22 Claims, 5 Drawing Sheets

IMAGING SCOPE WITH LEAK INDICATOR, AND RELATED IMAGING SYSTEM AND METHOD

TECHNICAL FIELD

The present disclosure generally relates to imaging scopes, imaging systems that include imaging scopes, and related methods. The present disclosure more particularly relates to imaging scopes with leak indicators, imaging systems that include imaging scopes with leak indicators, and related methods.

BACKGROUND

An imaging system having an imaging scope (e.g., an endoscope, an exoscope, etc.) and a camera can be used for capturing light reflected from an object, converting the captured light into a digital image, and displaying the digital image on a monitor. Endoscopes are used to illuminate and observe an internal portion of a patient's body during a medical procedure, whereas exoscopes are used to illuminate and observe a portion of a patient's body from a working distance away from the patient's body (e.g., 25-75 cm).

Imaging scopes are typically manufactured to be reused for multiple procedures and to withstand sterilization after each use. During sterilization, a reusable imaging scope will typically be subjected to high temperature steam (e.g., steam greater than 130° C.) for long periods of time (e.g., 1-2 hours). The steam and other cleaning materials used during sterilization can have a degrading effect on sealing portions of the imaging scope. Leaks in the imaging scope create the risk that the imaging scope will not be able to withstand exposure to high temperature steam during sterilization. They also create the risk that infectious material will enter the unsealed internal portion of the imaging scope and be passed to another patient during a subsequent medical procedure. For these and other reasons, reusable imaging scopes frequently undergo refurbishment and testing for leaks.

Imaging scopes are commonly tested for leaks via a technique that involves pumping air into the imaging scope or creating a partial vacuum in the imaging scope, and then using a pressure gauge to check whether or not the pressure within the imaging scope remains constant over time. Although this method is relatively simple, there are several drawbacks. For example, deterioration of the pressure gauge tube can cause false leak detection. Also, it can be difficult for a user to read and detect changes on the pressure gauge over time.

Another common leak testing technique includes dunking a pressurized imaging scope in a water tank and checking for the release of air bubbles. This technique can be problematic in that a water tank is required, the dunking step can be cumbersome, and it can be difficult to observe air bubbles associated with a small leak.

Aspects of the present invention are directed to these and other problems.

SUMMARY

According to an aspect of the present invention, an imaging scope includes an internal surface defining an internal cavity, a window permitting visual inspection of the internal cavity, a fluid in the internal cavity having a pressure different than ambient pressure, and an indicator positioned within the internal cavity and transitionable between nonvisible and visible through the window when the pressure of the fluid changes toward ambient pressure.

According to another aspect of the present invention, an imaging system includes an imaging scope and a camera. The imaging scope is configured to illuminate an object and capture light reflected from the object. The imaging scope includes an internal surface defining an internal cavity, a window permitting visual inspection of the internal cavity, a fluid in the internal cavity having a pressure different than ambient pressure, and an indicator positioned within the internal cavity and transitionable between nonvisible and visible through the window when the pressure of the fluid changes toward ambient pressure. The camera includes a light sensor with a light-sensitive surface configured to receive the captured light from the imaging scope, and generate a digital image representative of the captured light.

According to another aspect of the present invention, a method for detecting a leak in an imaging scope includes the steps of: positioning an indicator within an internal cavity of the imaging scope, the indicator transitionable positioned within the internal cavity and between nonvisible and visible through a window of the imaging scope when pressure of a fluid in the internal cavity changes toward ambient pressure; sealing the internal cavity from a surrounding environment; detecting transition of the indicator between nonvisible and visible; and based on completion of the detecting step, determining that a leak developed in the imaging scope.

In addition to, or as an alternative to, one or more of the features described above, further aspects of the present invention can include one or more of the following features, individually or in combination:

the indicator is within the internal cavity and is positionally fixed relative to the window;

the indicator is within the internal cavity and is movable relative to the window;

the imaging scope further includes a biaser transitionable between a first state and a second state when the pressure of the fluid changes toward ambient pressure;

the indicator transitions between nonvisible and visible through the window when the biaser transitions between the first and second states;

the biaser is a spring having a first length in the first state and a second length in the second state, the first length and the second length having different magnitudes;

the indicator transitions between nonvisible and visible when a position of the biaser relative to the window changes;

the biaser is an elastic volume container having a first volume in the first state and a second volume in the second state, the first volume and the second volume having different magnitudes;

the indicator transitions between nonvisible and visible when a volume of the biaser relative to the window changes;

the biaser covers the indicator at ambient pressure in the internal cavity;

the biaser exposes the indicator at ambient pressure in the internal cavity;

the imaging scope further includes an indicator housing extending between a first end and an opposing second end, the first end defining an opening to the internal cavity, and the second end defined by a base adjustably positioned relative to the first end;

the indicator housing has an indicator housing axis extending between the first end and the second end thereof, and the indicator is disposed within the indicator housing and is moveable along the indicator housing axis during transition of the indicator between nonvisible and visible;

the indicator forms a seal with the indicator housing such that an indicator housing cavity defined between the indicator and the base is fluidly sealed from the internal cavity; and the indicator and the base of the indicator housing are connected by a spring that extends through the indicator housing cavity;

the indicator is not electrically powered;

the indicator is an analog pressure meter and provides an analog display via the window;

the internal surface is in a shaft of the imaging scope;

the internal surface is in a handle of the imaging scope;

the window at least partially defines an outer surface of the imaging scope;

the imaging scope further includes an opaque wall that at least partially forms the internal cavity;

the pressure of the fluid in the internal cavity is above ambient pressure during normal operation;

the pressure of the fluid in the internal cavity is below ambient pressure during normal operation; and the imaging system further includes a sensor circuit configured to measure the pressure of the fluid and generate a leak detection signal when the measured pressure changes toward ambient pressure, and a camera control unit configured to control operation of the imaging scope and the camera, the camera control unit configured to receive the leak detection signal from the circuit and prevent further use of the imaging scope until repair of the leak.

These and other aspects of the present invention will become apparent in light of the drawings and detailed description provided below.

DETAILED DESCRIPTION

Figure 1:
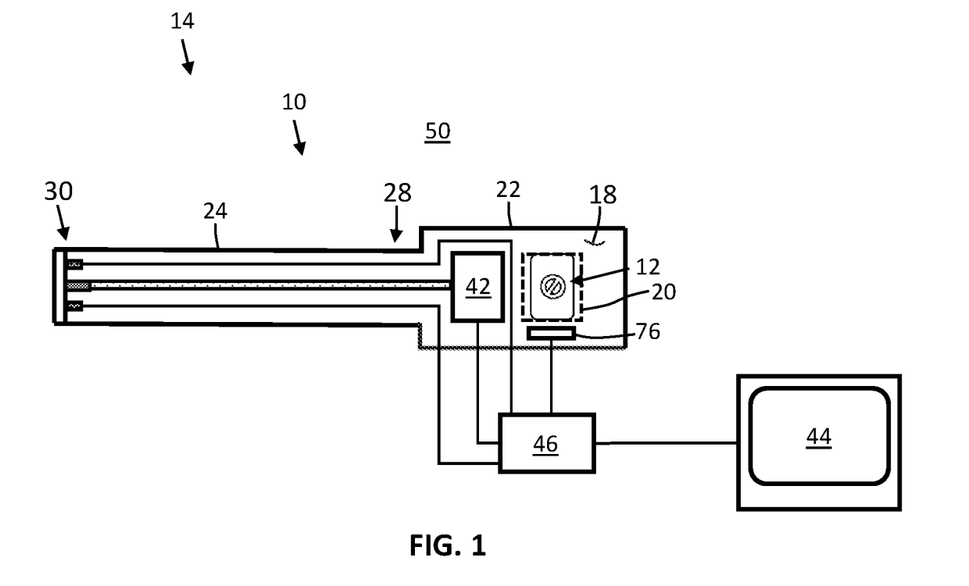
FIG. 1 schematically illustrates an imaging system including an imaging scope with a leak indicator.

Referring to FIG. 1, the present disclosure describes an imaging scope 10 (e.g., an endoscope, an exoscope, etc.) with a leak indicator 12 (hereinafter "indicator 12"), an imaging system 14 including the imaging scope 10 with the indicator 12, and a related method.

Referring to FIGS. 1, 4-7, and 9-12, the imaging scope 10 includes an internal surface 16 defining an internal cavity 18, a window 20 permitting visual inspection of the internal cavity 18, a fluid in the internal cavity 18 having a pressure different than ambient pressure, and an indicator 12 positioned within the internal cavity 18 and transitionable between nonvisible and visible through the window 20 when the pressure of the fluid changes toward ambient pressure.

Figure 2:
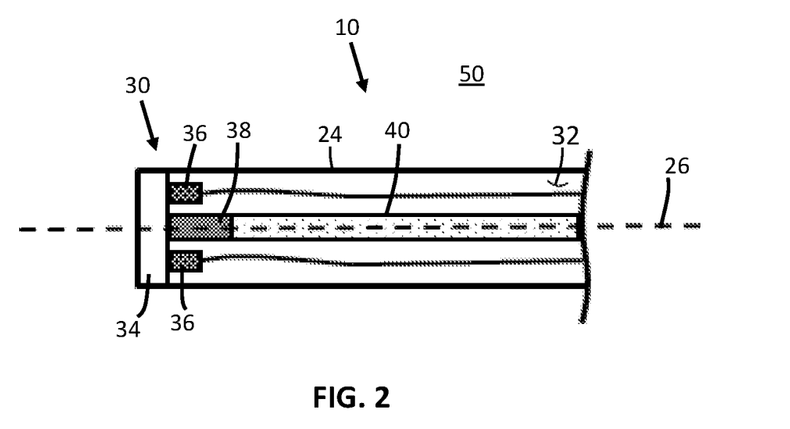
FIG. 2 schematically illustrates a portion of the imaging scope of FIG. 1.

The imaging scope 10 can have various configurations depending on the particular application. Referring to FIGS. 1 and 2, in the illustrated embodiment, the imaging scope 10 is a reusable endoscope intended for use in medical procedures. The imaging scope 10 includes a handle 22 and a shaft 24 extending therefrom. The shaft 24 extends along a longitudinal shaft axis 26 between a proximal end 28 and a distal end 30 of the shaft 24, and defines a shaft channel 32 extending therethrough. The distal end 30 of the shaft 24 includes a fluid-tight distal window 34 made of glass or another suitable material that is at least substantially transparent. The imaging scope 10 further includes a plurality of light sources 36 (e.g., LEDs) and an objective 38 positioned within the shaft channel 32 proximate the distal window 34. The light sources 36 selectively illuminate an object by selectively emitting illumination light through the distal window 34 and out of the distal end 30 of the shaft 24. The objective 38 captures light reflected from the object through the distal window 34, and an image transmission device 40 (e.g., a rod lens system) transmits the captured light from the objective 38 to a camera 42 that generates a digital image representative of the captured light.

Referring to FIG. 1, in the illustrated embodiment, the imaging scope 10 is a component of an imaging system 14 that additionally includes a monitor 44 and a camera control unit (CCU) 46 that selectively activates and deactivates the light sources 36 and processes the digital image received from the camera 42 for display on the monitor 44. The camera 42 is housed within the handle 22 of the imaging scope 10, and the CCU 46 is remotely positioned relative to the imaging scope 10 and the monitor 44. In other embodiments, the camera 42 can be housed within a camera head detachably coupled to the proximal end 28 of the shaft 24 of the imaging scope 10, and/or the CCU 46 can be incorporated into another component of the imaging system 14 (e.g., the handle 22, a camera head, the monitor 44).

The internal cavity 18 in which the indicator 12 is disposed can be in various parts of the imaging scope 10 depending on the particular application. Referring to FIG. 1, in the illustrated embodiment, the internal cavity 18 and the indicator 12 are in the handle 22 of the imaging scope 10, which is formed in part by the window 20 and a surrounding wall 48. The wall window 20 is at least translucent (i.e., translucent or transparent) and the wall 48 is opaque. The window 20 and the wall 48 have respective internal surfaces that partially define the internal cavity 18 of the imaging scope 10, and respective outer surfaces that partially define the exterior of the handle 22. In the illustrated embodiment, the internal cavity 18 within the handle 22 is in fluid communication with the shaft channel 32 that houses various components of the imaging scope 10, such as the objective 38, the LEDs 36, and the image transmission device 40. As such, the pressure within the internal cavity 18 is at least substantially equal to the pressure within the shaft channel 32. In other embodiments not shown in the drawings, the indicator 12 is disposed in the shaft channel 32 or another portion of the imaging scope 10.

The indicator 12 functions as an analog pressure meter that provides an analog display via the window 20. The indicator 12 is not electrically powered. The indicator 12 provides a user with real-time notification regarding a change in the pressure of the fluid within the internal cavity 18 toward ambient pressure (i.e., a change toward the pressure of the surrounding environment 50), which is indicative of the development of a leak in the imaging scope 10. During the development of a leak, the internal cavity 18 of the imaging scope 10 fluidly connects with the surrounding environment 50 and initiates a pressure equilibration therebetween. The pressure equilibration causes the pressure of the fluid within the internal cavity 18 to change toward ambient pressure.

In some embodiments, the imaging scope 10 further includes a biaser 52 transitionable between first and second states when the pressure of the fluid changes toward ambient pressure. In such embodiments, the biaser is configured such that transition between the first and second states causes transition of the indicator 12 between the nonvisible and visible states. In some embodiments (see FIGS. 4-5 and 9-10), the biaser 52 is a spring 54 having a first length in the first state and a different second length in a second state, and transition of the biaser 52 between the first and second lengths causes the indicator 12 to change between the nonvisible and visible states. In other embodiments (see FIGS. 11-12), the biaser 52 is an elastic volume container 56 (e.g., a balloon) having a first volume in the first state and a different second volume in the second state, and transition of the biaser 52 between the first and second volumes causes the indicator 12 to change between the nonvisible and visible states.

The imaging scope 10 can include various additional components that work together with the biaser 52 to facilitate transition of the indicator 12 between the nonvisible and visible states. For example, in the embodiments of FIGS. 4-7 and 9-12, the imaging scope 10 further includes an indicator housing 58 with an indicator housing axis extending between first and second ends 60, 62 of the indicator housing 58. The indicator housing axis extends in a direction parallel to a longitudinal axis of the imaging scope 10 (e.g., the shaft axis 26). The first end 60 of the indicator housing 58 defines an opening to the internal cavity 18, and the second end 62 of the indicator housing 58 is formed by a base 66. The position of the base 66 relative to the window 20 can be adjusted to calibrate the indicator 12 (e.g., to ensure alignment of the indicator 12 with the window 20 when in the visible state).

In some embodiments, the indicator 12 is movable relative to the window 20 during transition between the nonvisible and visible states. For example, in the embodiments of FIGS. 4-5 and 9-10, the indicator 12 is a flag member 68 and the biaser 52 is a spring 54. The flag member 68 includes a leak warning icon 70 and is moveable within the indicator housing 58 during transition between the nonvisible and visible states. The flag member 68 forms a seal with the indicator housing 58 such that an indicator housing cavity 72 defined between the flag member 68 and the base 66 is fluidly sealed from the internal cavity 18 of the imaging scope 10. In some embodiments, including those of FIGS. 4-5 and 9-10, a sealing member 73 is positioned between the flag member 68 and the spring 54, and aids in fluidly sealing the indicator housing cavity 72 from the internal cavity 18 of the imaging scope 10. The flag member 68 and the base 66 of the indicator housing 58 are connected by a spring 54 that extends through the indicator housing cavity 72. The position of the flag member 68 along the indicator housing axis changes (and thus the position of the flag member 68 relative to the window 20 changes) as the pressure in the internal cavity 18 of the imaging scope 10 changes.

Figure 6:
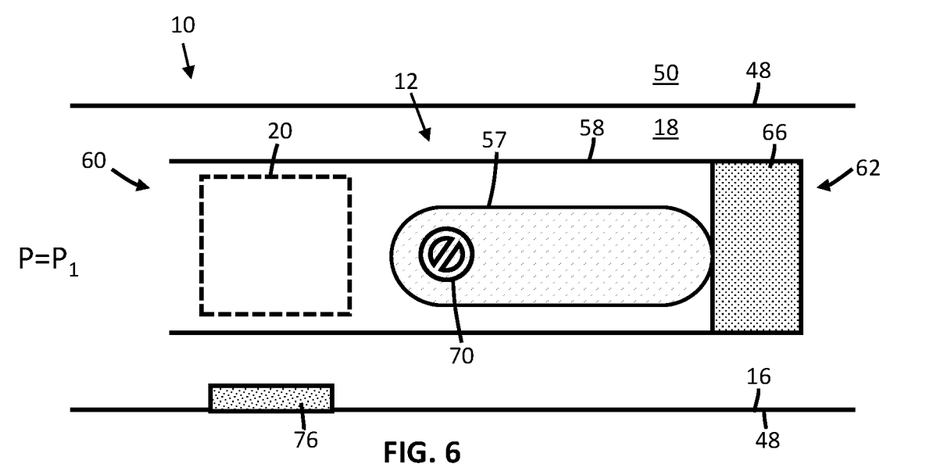
FIGS. 6 and 7 schematically illustrate a portion of another imaging scope, showing the indicator in nonvisible and visible states, respectively.
Figure 7:
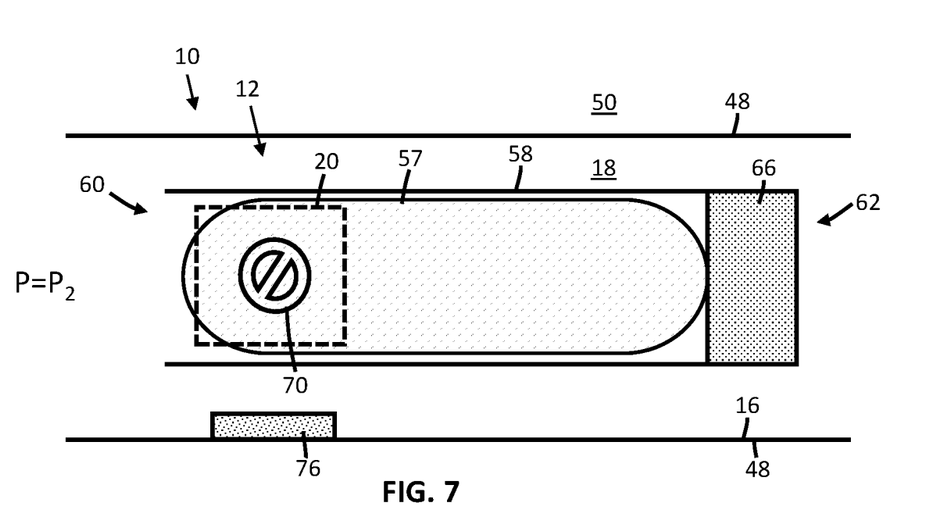

In the embodiment of FIGS. 6-7, the indicator 12 is an elastic volume container 57 disposed within the indicator housing 58. The elastic volume container 57 includes a leak warning icon 70 and is attached to the base 66 of the indicator housing 58. The volume of the elastic volume container 57 changes (and thus the position of the elastic volume container 57 relative to the window 20 changes) as the pressure in the internal cavity 18 of the imaging scope 10 changes.

Figure 11:
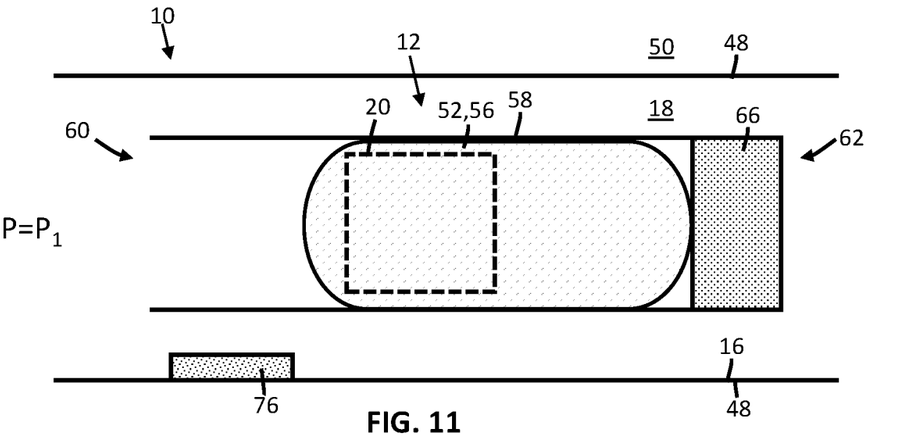
FIGS. 11 and 12 schematically illustrate a portion of another imaging scope, showing the indicator in nonvisible and visible states, respectively.
Figure 12:
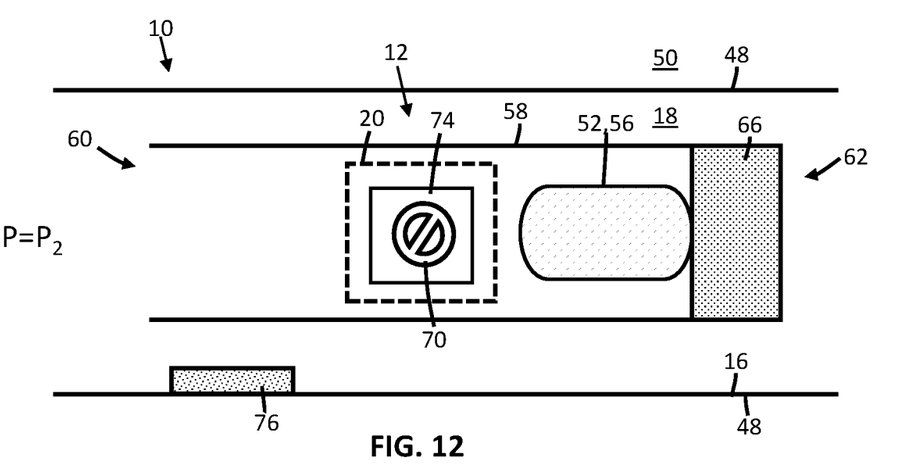

In some embodiments, the indicator 12 remains positionally fixed relative to the window 20, and transition of the indicator 12 between the nonvisible and visible states involves exposing or covering from view the indicator 12 using the biaser 52. In the embodiment of FIGS. 11 and 12, for example, the indicator 12 is a wall portion 74 of the indicator housing 58 having a leak warning icon 70 disposed thereon. In the nonvisible state (see FIG. 11), the indicator 12 is covered by the elastic volume container 56 such that it cannot be viewed by a user through the window 20. In the visible state (see FIG. 12), the indicator 12 is not covered by the elastic volume container 56, and thus can be viewed by a user through the window 20.

Figure 3:
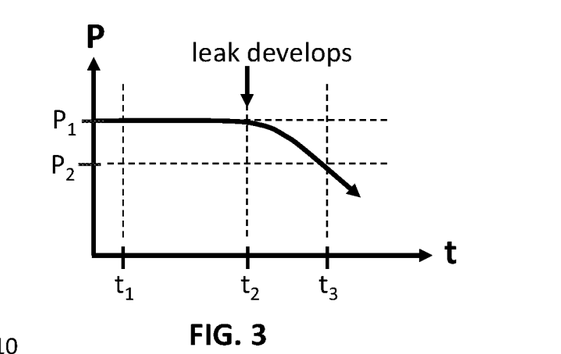
FIG. 3 plots internal pressure of the imaging scope of FIG. 1 versus time.
Figure 4:
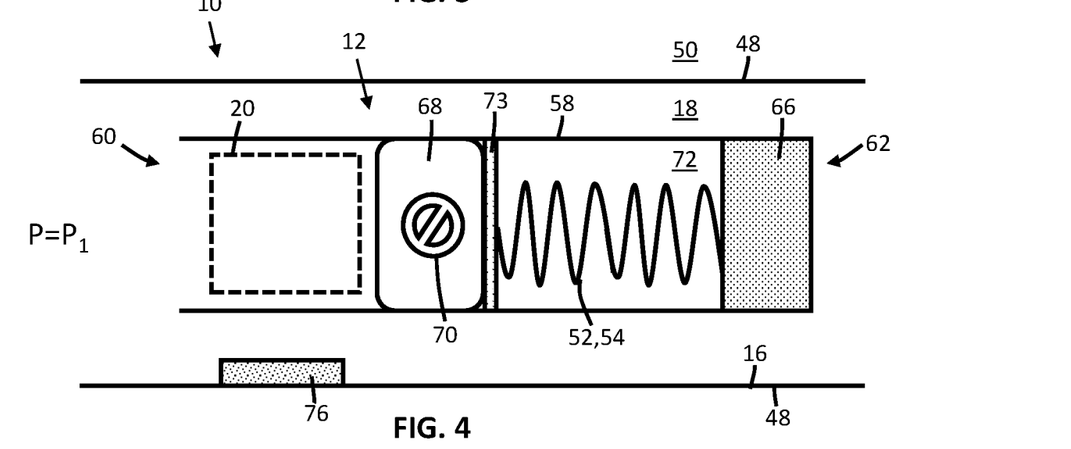
FIGS. 4 and 5 schematically illustrate a portion of the imaging scope of FIG. 1, showing the indicator in nonvisible and visible states, respectively.
Figure 5:
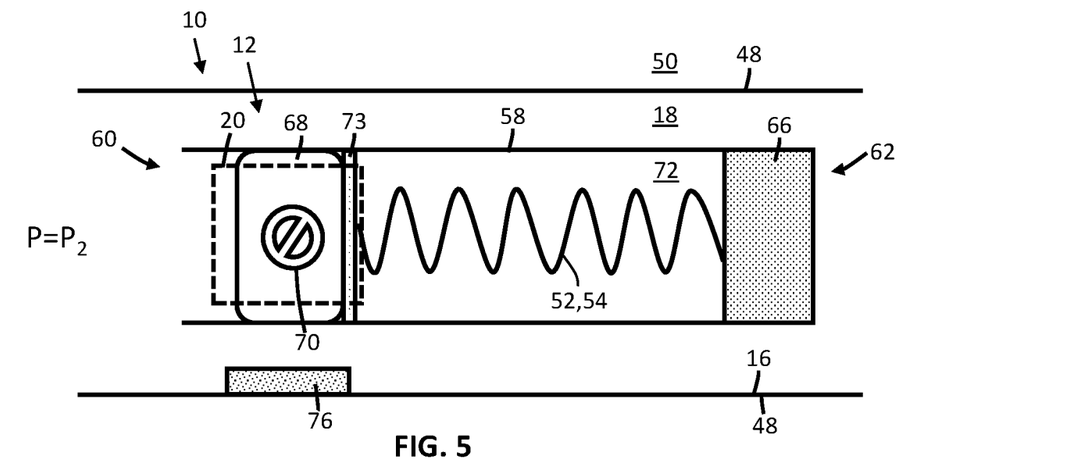
Figure 8:
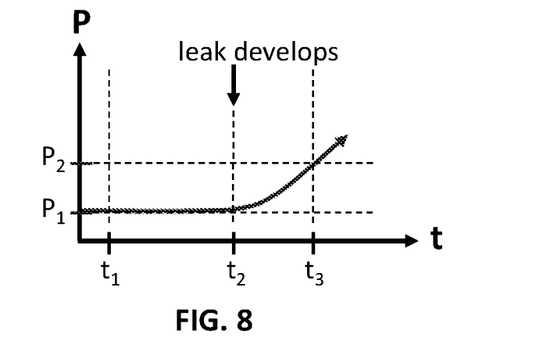
FIG. 8 plots internal pressure of another imaging scope versus time.
Figure 9:
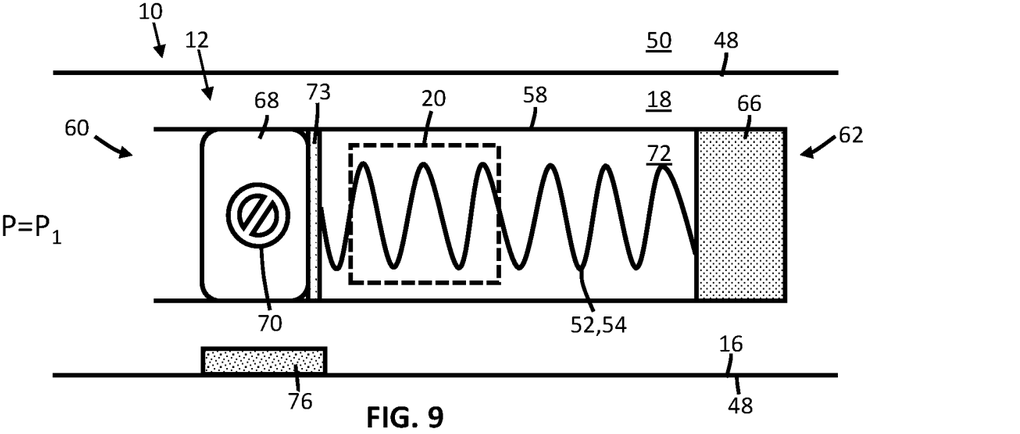
FIGS. 9 and 10 schematically illustrate a portion of an imaging scope, showing the indicator in nonvisible and visible states, respectively.
Figure 10:
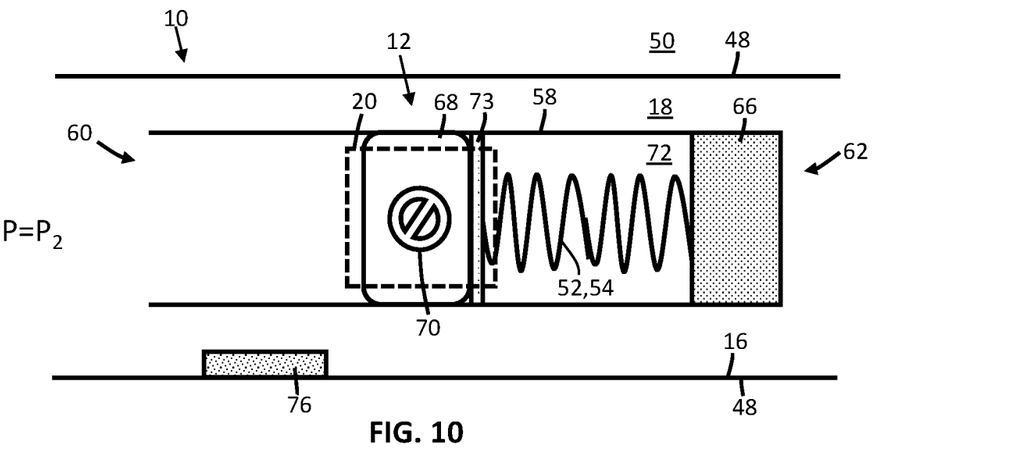

The configuration of the indicator 12 can vary based on whether (i) the pressure of the fluid in the internal cavity 18 has a static pressure that is above ambient pressure during normal operation of the imaging scope 10, or (ii) the pressure of the fluid in the internal cavity 18 has a static pressure that is below ambient pressure during normal operation of the imaging scope 10. In some embodiments (see FIGS. 4-7), the fluid in the internal cavity 18 is a gas (e.g., Helium) having a pressure above ambient pressure. FIG. 3 shows that when a leak develops in these types of gas-filled imaging scopes, the pressure of the fluid in the internal cavity 18 begins to decrease until it reaches equilibrium with ambient pressure. In other embodiments (see FIGS. 9-12), the internal cavity 18 of the imaging scope 10 is at a partial vacuum pressure during normal operation. In such embodiments, the pressure of the fluid in the internal cavity 18 is below ambient pressure during normal operation. FIG. 8 shows that when a leak develops in these types of vacuum-sealed imaging scopes, the pressure of the fluid in the internal cavity 18 begins to increase until it reaches equilibrium with ambient pressure.

In some embodiments, such as those in which the pressure of the fluid in the internal cavity 18 is above ambient pressure during normal operation (see FIGS. 4-5), the biaser 52 is never visible through the window 20. In other embodiments, the biaser 52 is visible through the window 20 when the indicator 12 is in the nonvisible state (see FIGS. 9 and 11).

In some embodiments, rather than having a leak warning icon 70 disposed thereon, the indicator 12 can have a leak warning color (e.g., red). Referring to FIGS. 11 and 12, for example, the elastic volume container 56 could be green and the indicator 12 (i.e., the wall portion 74 of the indicator housing 58) could be red. In such embodiments, when the indicator 12 is in the nonvisible state (i.e., covered by the elastic volume container 56), a user will view the green elastic volume container 56 through the window 20, and when the indicator 12 is in the visible state (i.e., not covered by the elastic volume container 56), the user will view the red indicator 12 through the window 20. The user would intuitively understand green to mean that no leak is present, and would intuitively understand red to mean that a leak is present.

Referring to FIGS. 1, 4-7, and 9-10, in some embodiments the imaging system 14 further includes a sensor circuit 76 configured to measure the pressure of the fluid within the internal cavity 18 and generate a leak detection signal when the measured pressure changes towards ambient pressure. In such embodiments, the CCU 46 is configured to control operation of the imaging scope 10 and the camera 42, and the CCU 46 is configured to receive the leak detection signal from the sensor circuit 76 and prevent further use of the imaging scope 10 until repair of the leak.

According to another aspect of the present invention, a method for detecting a leak in the imaging scope 10 includes the steps of: positioning the indicator 12 within the internal cavity 18 of the imaging scope 10; sealing the internal cavity 18 from the surrounding environment 50; detecting transition of the indicator 12 between the nonvisible and visible states; and based on completion of the detecting step, determining that a leak developed in the imaging scope 10.

The present disclosure describes aspects of the invention with reference to the exemplary embodiments illustrated in the drawings; however, aspects of the invention are not limited to the exemplary embodiments illustrated in the drawings. It will be apparent to those of ordinary skill in the art that aspects of the invention include many more embodiments. Accordingly, aspects of the invention are not to be restricted in light of the exemplary embodiments illustrated in the drawings. It will also be apparent to those of ordinary skill in the art that variations and modifications can be made without departing from the true scope of the present disclosure. For example, in some instances, one or more features disclosed in connection with one embodiment can be used alone or in combination with one or more features of one or more other embodiments.

What is claimed is:

1. An imaging scope, comprising:
    an internal surface defining an internal cavity;
    a window permitting visual inspection of the internal cavity;
    a gas in the internal cavity having a pressure different than an ambient pressure of an environment surrounding the imaging scope;
    an indicator positioned within the internal cavity and transitionable between nonvisible and visible through the window when the pressure of the gas changes toward the ambient pressure; and
    a biaser transitionable between a first state and a second state when the pressure of the gas changes toward the ambient pressure;
    wherein the biaser moves relative to the window during transition of the indicator between nonvisible and visible.

2. The imaging scope of claim 1, wherein the indicator is positionally fixed relative to the window during transition between nonvisible and visible.

3. The imaging scope of claim 1, wherein the indicator moves relative to the window during transition between nonvisible and visible.

4. The imaging scope of claim 1, wherein the biaser is a spring having a first length in the first state and a second length in the second state, the first length and the second length having different magnitudes.

5. The imaging scope of claim 1, wherein the indicator transitions between nonvisible and visible when the biaser moves relative to the window.

6. The imaging scope of claim 1, wherein the biaser is an elastic volume container having a first volume in the first state and a second volume in the second state, the first volume and the second volume having different magnitudes.

7. The imaging scope of claim 1, wherein the indicator transitions between nonvisible and visible when a volume of the biaser changes.

8. The imaging scope of claim 1, wherein the biaser covers the indicator when a pressure in the internal cavity is at the ambient pressure of the environment surrounding the imaging scope.

9. The imaging scope of claim 1, wherein the biaser exposes the indicator when a pressure in the internal cavity is at the ambient pressure of the environment surrounding the imaging scope.

10. The imaging scope of claim 1, further including an indicator housing extending between a first end and an opposing second end, the first end defining an opening to the internal cavity, and the second end defined by a base adjustably positioned relative to the first end.

11. The imaging scope of claim 1, wherein the indicator is not electrically powered.

12. The imaging scope of claim 1, wherein the indicator is an analog pressure meter and provides an analog display via the window.

13. The imaging scope of claim 1, wherein the internal surface is in a shaft of the imaging scope.

14. The imaging scope of claim 1, wherein the internal surface is in a handle of the imaging scope.

15. The imaging scope of claim 1, wherein the window at least partially defines an outer surface of the imaging scope.

16. The imaging scope of claim 1, further comprising an opaque wall that at least partially forms the internal cavity.

17. The imaging scope of claim 1, wherein the pressure of the gas in the internal cavity is above the ambient pressure during normal operation.

18. The imaging scope of claim 1, wherein the pressure of the gas in the internal cavity is below the ambient pressure during normal operation.

19. An imaging scope, comprising:
    an internal surface defining an internal cavity;
    a window permitting visual inspection of the internal cavity;
    a fluid in the internal cavity having a pressure different than an ambient pressure of an environment surrounding the imaging scope;
    an indicator positioned within the internal cavity and transitionable between nonvisible and visible through the window when the pressure of the fluid changes toward the ambient pressure; and
    an indicator housing extending between a first end and an opposing second end, the first end defining an opening to the internal cavity, and the second end defined by a base adjustably positioned relative to the first end;
    wherein the indicator housing has an indicator housing axis extending between the first end and the second end thereof; and
    wherein the indicator is disposed within the indicator housing and is moveable along the indicator housing axis during transition of the indicator between nonvisible and visible.

20. The imaging scope of claim 19, wherein the indicator forms a seal with the indicator housing such that an indicator housing cavity defined between the indicator and the base is fluidly sealed from the internal cavity; and
    wherein the indicator and the base of the indicator housing are connected by a spring that extends through the indicator housing cavity.

21. An imaging system, comprising:
    an imaging scope configured to illuminate an object and capture light reflected from the object, the imaging scope including:

an internal surface defining an internal cavity;

a window permitting visual inspection of the internal cavity;

a gas in the internal cavity having a pressure different than an ambient pressure of an environment surrounding the imaging scope;

an indicator positioned within the internal cavity and transitionable between nonvisible and visible through the window when the pressure of the gas changes toward the ambient pressure; and a biaser transitionable between a first state and a second state when the pressure of the gas changes toward the ambient pressure;

wherein at the biaser moves relative to the window during transition of the indicator between nonvisible and visible;

a camera having a light sensor with a light-sensitive surface configured to receive the captured light from the imaging scope, and generate a digital image representative of the captured light.

22. The imaging system of claim 21, further comprising a sensor circuit configured to measure the pressure of the gas and generate a leak detection signal when the measured pressure changes toward the ambient pressure;

a camera control unit configured to control operation of the imaging scope and the camera, the camera control unit configured to receive the leak detection signal from the circuit and prevent further use of the imaging scope until repair of the leak.

* * * * *